United States Patent [19]

Rutenberg et al.

[11] Patent Number: 5,287,272

[45] Date of Patent: Feb. 15, 1994

[54] AUTOMATED CYTOLOGICAL SPECIMEN CLASSIFICATION SYSTEM AND METHOD

[75] Inventors: Mark R. Rutenberg, Monsey, N.Y.; Thomas L. Hall, Pasadena, Calif.; Robert Domes, Newbury Park, Calif.; Richard Chaban, Ventura, Calif.; Thomas Dulak, Newhall, Calif.; James M. Herriman; John Porzio, both of New York, N.Y.; Randall L. Luck, Brooklyn, N.Y.; James Knapp, New York, N.Y.

[73] Assignee: Neuromedical Systems, Inc., Suffern, N.Y.

[21] Appl. No.: 420,105

[22] Filed: Oct. 11, 1989

Related U.S. Application Data

[63] Continuation-in-part of Ser. No. 179,060, Apr. 8, 1988, Pat. No. 4,965,725.

[51] Int. Cl.$^5$ .................... G06F 15/18; G06F 15/42; G06K 9/62
[52] U.S. Cl. .................... 364/413.01; 382/15; 382/36
[58] Field of Search ............... 364/413.1, 413.2, 413.8, 364/413.9, 801, 807; 382/6, 15, 36

[56] References Cited

U.S. PATENT DOCUMENTS

| | | | |
|---|---|---|---|
| 3,333,248 | 7/1967 | Greenberg et al. | 340/172.5 |
| 4,000,417 | 12/1976 | Adkisson et al. | 250/201 |
| 4,048,616 | 9/1977 | Hart et al. | 340/146.3 |
| 4,404,683 | 9/1983 | Kobayashi et al. | 382/6 |
| 4,501,495 | 2/1985 | Faulkner et al. | 356/244 |
| 4,513,438 | 4/1985 | Graham et al. | 382/6 |
| 4,591,980 | 5/1986 | Huberman et al. | 364/200 |
| 4,612,614 | 9/1986 | Deindoerfer et al. | 364/413.1 |
| 4,700,298 | 12/1986 | Palcic et al. | 364/413.1 |
| 4,705,630 | 11/1987 | Gordon et al. | 210/361 |
| 4,805,225 | 2/1989 | Clark | 382/15 |
| 4,807,979 | 2/1989 | Saccomanno et al. | 350/520 |
| 4,821,118 | 4/1989 | LaFreniere | 358/108 |
| 4,833,625 | 5/1989 | Fisher et al. | 358/111 |
| 4,965,725 | 10/1990 | Rutenberg | 364/413.1 |

FOREIGN PATENT DOCUMENTS

WO89/09969 10/1989 PCT Int'l Appl.
203586 2/1982 United Kingdom.

OTHER PUBLICATIONS

Tanaka et al, Automated Cytologic Screen System Dec. 1982, pp. 229-285.
"'Yellow IRIS' Urinalysis Workstation", Deindoerfer et al., Clinical Chemistry, vol. 31, No. 9, pp. 1491-1499 (1985).
U.S. patent application Ser. No. 07/425,665, filed Oct. 23, 1989; Automated Cytological Specimen Classification System and Method.
U.S. patent application Ser. No. 07/502,611, filed Mar. 30, 1990; Automated Cytological Specimen Classification System and Method.
Cybest Model 3, Automated Cytologic Screening System for Uterine Cancer Utilizing Image Analysis Processing; Tanaka, et al.
Hybrid Holographic-Digital Processing System of Three-Dimensional Displacement Measurement, Vlad et al.
Astigmatic Holographic Processor for Local Pattern Recognition, Rabal et al. Inspect abstract.
Diagnostic Cytology and Its Histopathologic Bases, pp. 1152 and 1153, Leopold G. Koss, M.D.
Vlad Inspec Abstract, Proceedings of the SPIE-The International Soc. for Optical Eng., vol. 700 pp. 344-351.
Megla, SID Journal, vol. 11, No. 5, Sep.-Oct. 1974 pp. 20-22.

(List continued on next page.)

*Primary Examiner*—Roy N. Envall, Jr.
*Assistant Examiner*—A. Bodendorf
*Attorney, Agent, or Firm*—Renner, Otto, Boisselle & Sklar

[57] ABSTRACT

An automated screening system and method for cytological specimen classification in which a neural network is utilized in performance of the classification function. Also included is an automated microscope and associated image processing circuitry.

27 Claims, 5 Drawing Sheets

OTHER PUBLICATIONS

Mizuno, H., "A Neural Network Model for Pattern Recognition" Proceedings of the Third International Workshop on Parallel Processing by Cellular Automats & Arrays, Berlin, GDR, Sep. 9-11, 1986 pp. 234-241.

Minsky et al., "Perceptrons", 1988.

Rumelhart et al., "Parallel Distributed Processing", vol. 1, 1986 The Massachusetts Institute of Technology.

D. Tien et al., "Automated Cervical Smear Classification" IEEE/Ninth Annual Conf. of Engr. in Medicine & Biology Soc., 1457, 1987.

Hecht-Nielsen, "Neurocomputing: Picking the Human Brain" IEEE Spectrum, Mar. 1988.

Richard P. Lippmann, "An Introduction to Computing with Neural Nets", IEEE ASSP Magazine, Apr. 1987.

D. L. Rosenthal, "Automation of Uterine Cervical Cytology: Accomplishments and Goals", 1986 Elsevier Science Publishers pp. 65-72.

Hall et al., "Biology of Disease, Applications of Quantitative Microscopy in Tumor Pathology" Laboratory Investigation, vol. 53, No. 1, p. 5, 1985.

Hall et al., "Microcomputer-based Image Processing Work-stations for Cytology", Applied Optics, vol. 26, No. 16, Aug. 1987.

Rosenthal Abstract, "Critical Review of Potential of Neural Nets in Diagnostic Pathology" Abstract only.

Egbert et al., "Preprocessing of Biomedical Images for Neuralcomputer Analysis", University of Nevada Reno, pp. I-561-I568.

Imasato et al, "Cybest—Automated Pap Smear Pre-screener" Toshiba Review, No. 100, Nov.-Dec. 1975.

K. Fukushima, "Self-organizing Neural Network Models for Visual Pattern Recognition" Acta Neurochirurgica, Suppl. 41. 51-67 (1987).

Oldham et al. Abstract, "Neural Network Recognition of Mammographic Lesions".

Dayhoff et al. Abstract, "Segmentation of True Color Microscopic Images Using a Back Propogation Neural Network".

Pao, "Adaptive Pattern Recognition and Neural Networks", 1989 Addison-Wesley Publishing Company, Inc.

Kunihiko Fukushima, "Neural Network Model for Selective Attention in Visual Pattern Recognition and Associative Recall", 1987, vol. 26, No. 23/Applied Optics.

AUTOMATED CYTOLOGICAL SPECIMEN CLASSIFICATION SYSTEM AND METHOD

This application is a continuation-in-part of U.S. patent application Ser. No. 179,060, filed Apr. 8, 1988, now U.S. Pat. No. 4,965,725 the entire disclosure of which is hereby incorporated by reference.

TECHNICAL FIELD

This invention relates generally, as indicated, to cell classification and, more particularly, to a system for increasing the speed and accuracy of cervical smear analysis.

BACKGROUND OF THE INVENTION

The examination of a cervical smear by what often is referred to as a Pap test is a mass screening cytological examination which currently requires individual visual inspection by a person of virtually all of the approximately 100,000 cells on a typical slide. The test, therefore, suffers from a high false negative rate due to the tedium and fatigue associated with this requirement for exhaustive search.

Prompted by the clear commercial potential for automated cervical smear analysis, several attempts to this end have been made heretofore. These attempts have proven to be unsuccessful at least partly because they could not accommodate overlapping cells as are typically found in the Pap smear. To circumvent the classification problems created by overlapping cells, specialized "monolayer preparations" have been prepared. A monolayer preparation is a specially prepared smear in which the cervical cells are centrifuged and filtered so that only a single layer of cells results. Besides serious cell preservation and cell transportation problems, the expense and time involved in the monolayer preparation precludes its use as a population screening substitute for the Pap smear.

Even when limited to the non-overlapping cell images provided by the monolayer preparation, prior art attempts at automated cytological classification have not been able to process cervical smear images at anything close to manual processing time. Many of these attempts at automated cytological classification have relied on feature extraction algorithms which attempt to select and to measure some feature within the image, e.g., the shape of the cell necleus. Feature extraction algorithms have failed due to the inability to segment the image into the components which require measurement. One cannot measure nuclear size, for example, unless the image is segmented so that the cellular nuclei are identified. Template matching, in which an actual image (not a mathematical quantity) is compared with stored exemplar images also has not been successful since it is computationally intensive and the infinite variety of possible Pap smear images or scenes would require an excessive number of exemplar image comparisons. The distinction between feature extraction and template matching is outlined in the Collings reference on pages 1 through 5 while image segmentation techniques are discussed in Chapter 7 of the Gonzalez reference.

An example of the limitations of the prior art can be found in the 1987 reference entitled "Automated Cervical Screen Classification" by Tien et al, identified further below.

Background references of interest are, as follows:

Rumelhart, David E. and McClelland, James L., "Parallel Distributed Processing," MIT Press, 1986, Volume 1;

Tien, D. et al, "Automated Cervical Smear Classification," Proceedings of the IEEE/Ninth Annual Conference of the Engineering in Medicine and Biology Society, 1987, p. 1457-1458;

Hecht-Nielsen, Robert, "Neurocomputing: Picking the Human Brain," IEEE Spectrum, March, 1988, p. 36-41; and Lippmann, Richard P., "An Introduction to Computing with Neural Nets," IEEE ASSP Magazine, April, 1987, p. 4-22.

BRIEF SUMMARY OF THE INVENTION

An object of the invention is to automate at least part of the classification procedure for cytological specimens.

Another consistent objective is to provide semi-automation in a cytological specimen classification apparatus and method, whereby at least part of the cell classification procedure may be carried out by a human being.

Consistent with the foregoing, an object of the present invention is to classify cytological specimens into categories, for example, categories of diagnostic significance, and, more particularly, to automate at least a part of such classification procedure.

As used herein the term "automated" means that at least part of the apparatus is automated; in the preferred embodiment a portion of the method is carried out by a person.

Briefly, according to one embodiment, the invention includes an initial classifier (sometimes referred to as a primary classifier) preliminarily to classify a cytological specimen and a subsequent classifier (sometimes referred to as a secondary classifier) to classify those portions of the cytological specimen selected by the initial classifier for subsequent classification.

According to one embodiment, the invention includes an initial classifier (sometimes referred to as a primary classifier) preliminarily to classify a cytological specimen, a subsequent classifier (sometimes referred to as a secondary classifier) to classify those portions of the cytological specimen selected by the initial classifier for subsequent classification, and a tertiary classification to determine characteristics of or to classify those portions of the cytological specimen that are selected by the subsequent classifier for further classification.

In one embodiment the primary classifier performs a low level morphological feature screening function on the entire image while the secondary classifier performs a high level pattern matching identification on those images not screened out by the primary classifier.

In an embodiment of the invention the primary classifier classifies specimens according to size criteria and integrated optical density.

In an embodiment the secondary classifier is a neural net.

In an embodiment the tertiary classifier may be a person.

In an embodiment the present invention performs its classification of a group of specimens within the period of time typically consumed for this task by careful manual screening (i.e., approximately six minutes/specimen) or faster.

In an embodiment the present invention performs its classification on cytological specimens which contain the numbers and types of objects other than single layers of cells of interest that are typically found in cervical Pap smears (e.g., clumps of cells, overlapping cells, debris, clumps of leucocytes, bacteria, mucus).

In an embodiment the present invention performs the above-described classification on cervical smears for the detection of pre-malignant and malignant cells.

In an embodiment the present invention performs its classification with smaller false negative error rates than those typically found in conventional manual cervical smear screening.

In an embodiment of the present invention classification of cytological specimens into medically significant diagnostic categories will be more reliable, i.e., will have lower false negative error rates, than present methods.

In an embodiment the cytological classification system of the present invention does not require a modification in the procedure by which cellular specimens are obtained from the patient, i.e., standard Pap smears are used for its input.

In an embodiment the cytological classification system of the present invention will permit reliable classification within processing time constraints that permit economically viable operation.

In an embodiment of the invention classification of a cytological specimen is made by a person, and subsequent automated (or semi-automated) classification of selected specimens, such as those primarily noted as negative by such person, or, if desired, of all specimens, then may be carried out.

In an embodiment an automated specimen transfer mechanism is provided to transport cytological specimens between a storage location and an examination location.

In an embodiment of the invention a marking system marks selected areas of a cytological specimen at which prescribed characteristics appear, such marking being either automatically, semi-automatically or manually initiated.

In an embodiment of the invention classification of a cytological specimen is authorized if an authorized identification is associated with the specimen, and such classification may be prevented if such authorized identification is not found.

In an embodiment of the invention improvements are provided to an automated microscope, including, for example, one or more of focus control, light intensity control, positioning control, and lens or objective magnification changing.

These and other objects, advantages and features of the present invention will become evident to those of ordinary skill in the art after having read the following detailed description of the preferred embodiment.

It is noted here that the published articles cited herein are specifically incorporated by reference.

Moreover, it is noted here that the invention is described herein mainly with respect to classification of cytological specimens in the form of a cervical smear, as typically is done in connection with a Pap test. However, it will be appreciated that this is but one example of the application of the principles of the invention which may be used to classify other cytological specimens.

DESCRIPTION OF THE PREFERRED AND ALTERNATE EMBODIMENTS

Figures 1A, 1B:
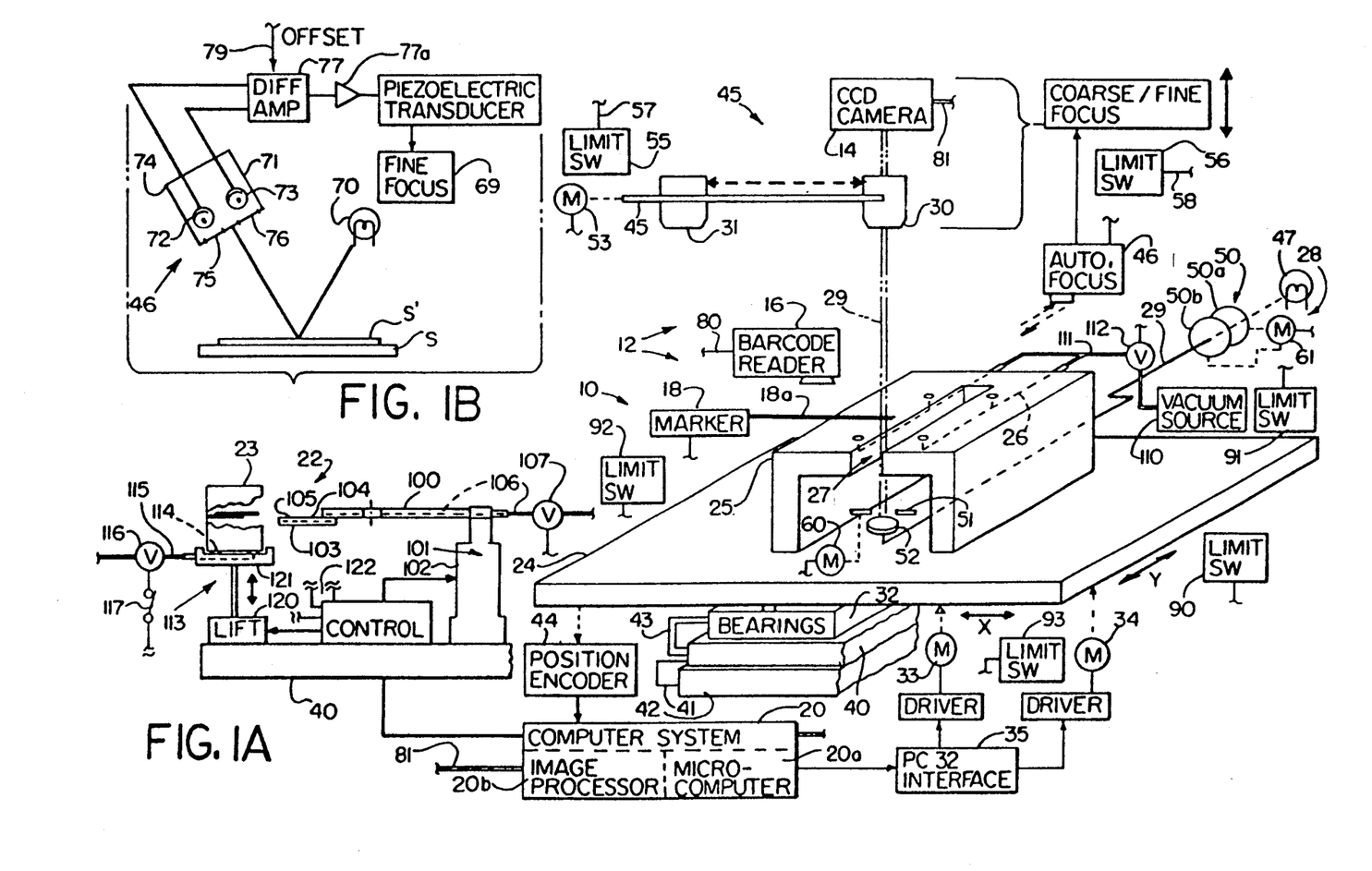
FIG. 1A is a schematic illustration of an automated cytological specimen classification system according to the invention.
FIG. 1B is a schematic illustration of the automatic fine focus adjustment of the system of FIG. 1A.

With reference to the drawings in which like reference numerals depict like items, and specifically to FIG. 1A, there is illustrated a neural network based automated cytological specimen classification (sometimes referred to as screening) screening device or system 10 in accordance with the present invention. The screening device 10 includes an automated microscope system 12, a camera 14, a barcode reader 16, a slide marker 18, and a computer processing system 20.

Briefly, the screening device 10 is used to classify cytological specimens, in the preferred embodiment to determine and/or to help to determine whether a cytological specimen contained on a slide S (or on or in some other support, container, etc.) includes characteristics or features of interest. Exemplary characteristics are those which are had by malignant or premalignant cells in what is commonly known as a Pap smear. In an exemplary embodiment described in detail below, the automated microscope system 12 makes a low resolution examination of the specimen during which some working parameters, such as the location of the specimen on the slide, focus, and/or illumination level (for optimum viewing in the subsequent high resolution examination), are determined. Authorization to conduct the examination, e.g., using the barcode reader 14 to sense whether the barcode on a slide is proper, also may be determined prior to or during the low resolution examination. Thereafter, with reliance on such working parameters and authorization, a high resolution examination of the specimen is made by the microscope system 12. Based on information obtained during such high resolution examination, primary, secondary and tertiary classification procedures are carried out to determine, for example, whether malignant or pre-malignant cells are contained in the specimen. Preferably the primary and secondary techniques are automated and the tertiary classification is carried out manually, i.e., by a person. However, consistent with the invention other types of primary, secondary and/or tertiary image processing techniques may be employed.

Operation of the system 10 is generally under the control of the computer system 20. Accordingly, such computer system includes a general purpose computer 20a, such as an AT type microcomputer, and an image processor 20b, such as one sold under the U.S. registered trademark PIPE by ASPEX INCORPORATED.

The automated microscope system 12 includes a number of elements designed to facilitate the quick and easy handling of specimen slides. One such element is a robotic slide handler 22 which, upon appropriate commands from the computer system 20, moves the specimen slides from a holder 23, called a cassette, to a motorized movable stage 24 for transport into and within the optical path of the microscope for cell classification, and then back to the cassette after classification. Mounted to (preferably bolted to) the motorized stage 24 is a slide support bridge (sometimes referred to as a tooling plate or tooling fixture) 25 upon which the slide is held for movement through the microscope system 12. The bridge 25 has one or more passages 26 (preferably four) in the area below where the slide is positioned and opening to face the slide to allow the creation of a vacuum under the slide to hold it firmly down upon and in place on the bridge. The tooling fixture bridge 25 also includes a relief area or slot 27 to allow the robotic slide handler 22 to grip the slide during placement on and removal from the tooling fixture bridge 25. The slot 27 also provides space for illuminating light from a light source 28 to travel along an optical path designated 29 to the microscope objectives 30, 31.

The motorized stage 24 is mounted upon cross roller bearings 32 and powered by two stepping motors 33, 34 with associated drivers by Compumotor together with a Parker Compumotor PC23 interface controller 35 to provide precise movement of the slide relative to the optical path 29 and viewing area of the microscope. The bearings 32 are mounted to the microscope base or frame 40, which in turn is attached by conventional springs and vibration damping shock absorbers 41 to a heavy (e.g., 500 pounds) granite base 42. Support of bearings 32 also may be by springs and/or shock absorbers 43.

The stage motors 33, 34 are controlled by the motor controller 44 (the mentioned PC23 interface) which converts commands from the computer processing system 20 into appropriate signals to cause the motors 33, 34 to move the stage to the prescribed locations. The precise location of the stage 24, and thus the slide, is detected by the position encoder 44. Such position encoder 44 may be a conventional device that produces pulses representative of movement or location of the stage. Those pulses, as is conventional, may be decoded by the computer system 20 to identify the current location of the stage 24, e.g., relative to a home or reference location or relative to some other location. An exemplary position encoder is sold by inch resolution by Heidenhain.

The automated microscope 12 also includes features to provide fast, precise imaging of each area and/or of selected areas of a slide positioned on the bridge 25, as is described further below. The optical system 45 of the automated microscope 12 includes an objective carriage 45, and an autofocusing mechanism 46. The light source 28 includes a lamp 47 of constant color temperature, light intensity control filters 50, an automated iris or diaphragm 51, and associated reflectors, prisms, lenses, light conductors, etc., schematically represented at 52, to send light along the optical path 29 to illuminate the specimen from below. (If desired, illumination of the specimen can be from above.)

The objective carriage 45 moves the appropriate magnification objective 30 and 31 (say, respectively, of 5X and 20X magnification), or lens system, into place in the optical path 29 to provide for low or high resolution viewing of the slide, respectively, as desired during the particular phase of operation. A motor 53 which is controlled via a connection 54 by the computer system 20 selectively moves the carriage 45 and respective objectives 30, 31 into the optical path 29. Limit switches 55, 56 sense maximum travel of the carriage 45 and cooperate with the computer system 20 in standard fashion to prevent over-travel of the carriage. A conventional adjustment 57 is schematically shown for parsontration, i.e., centering of the respective objectives 30, 31 in optical path 29 regardless of whether the carriage 45 has moved to position one or the other objectives in the optical path.

The autoiris 51, such as an adjustable aperture or diaphram, is for controlling the intensity of light transmitted to the slide and in the optical path 29 of the microscope 12 to the objectives 30, 31. The autoiris automatically adjusts the transmitted light intensity according to which objective 30, 31 the carriage 45 has positioned in the optical path 29. A motor 60 controlled by the computer system 20 adjusts the iris 51 to respective relatively more open and relatively more closed conditions at the same time that motor 53 moves the carriage 45 to place respective low and high resolution objectives in the optical path 29.

The filters 50 may be counter rotating variable neutral density linear polarizer filters 50a, 50b positioned in the optical path 29 between the light source 41 and the iris 51 to provide further control of the light intensity transmitted into the optical path without affecting the color temperature of the light. A motor 61 rotates the filters 50a, 50b under control of computer system 20, which may automatically call for an increase or a decrease in slide illumination intensity, e.g., as requested by a user, as the light source ages and/or is changed, etc. By rotating the polarizers 50a, 50b, the extent that they cross or are parallel and, thus, the amount of transmission therethrough can be controlled.

The automated microscope includes a coarse focus adjustment mechanism and a fine focus adjustment mechanism 69 (FIG. 1B), both being of conventional design, and, therefore, neither of which is shown in detail. The coarse focus adjustment may be operated by a micrometer type control that can be operated, e.g., turned manually. The fine focus adjustment also can be operated manually if desired. However, the fine focus adjustment preferably is operated automatically by the auto focus 46 in the manner described below. (Other types of focus adjustments also may be employed.)

As is seen in FIG. 1B, the auto focus 46 includes a light source 70, a bi-cell 71 (a device with two photocells or other photosensitive devices 72, 73 in a housing 74 with a mask formed by a pair of openings 75, 76 for guiding light to the respective photocells,) a differential amplifier 77 with an offset connection to the computer 20, a piezoelectric device 78, and a mechanical coupling 79 to the fine focus 69. Light from the source 70 is reflected off the top surface of the cover slip S' on slide S. The photosensors 72, 73 produce electrical outputs representing the position of the slide relative to the light source and the bi-cell 71. Differential amplifier 77 determines the difference between the photosensor outputs (it being desirable that such difference be minimized). An offset voltage can be provided via the computer and a digital to analog converter (not shown) to compensate for the thickness of the cover slip S' so that the actual point of focus is at the surface of the slide S or a desired depth into the specimen on the slide S. The output from the differential amplifier 77 may be further amplified by an amplifier 77a, and the output from such amplifier is used to provide a voltage input to the piezoelectric device 78. The piezoelectric device then mechanically operates the fine focus 69 control of the microscope 12 via the mechanical connection 79.

Another focus control for the microscope 12 also may be provided. Such focus control may rely on image processing, as is described further below, to determine the degree of focus that an object is seen by the camera 14 in particular. Such image processing focus control can be used both to make a focus map of the slide S and also to control the fine focus adjusting mechanism 69 and/or the coarse focus adjusting mechanism to bring the image into focus for the camera.

The image processing focusing described may be carried out during high and low resolution viewing. During low resolution viewing focal information is correlated with position coordinates from the position encoder 44 to compose a focal map, and the resulting focal map is stored in computer memory. During high resolution viewing, the computer system 20 provides the the focal information from the stored focal map in accordance with the location of the viewing field as determined by the position encoder 44 to adjust focus by mechanically controlling the coarse and/or fine focus adjustment mechanisms of the microscope 12. This allows for fast focusing during the high resolution scan.

Alternatively, focusing can be carried out during other portions of the low and/or high resolution examinations of the slide. As an example, the focusing function can be carried out prior to the initial low resolution examination of the slide and/or prior to the first high resolution examination of the slide. In the high resolution examination, as is described further below, several specific areas or "tiles" of the slide are examined, and focusing function can be carried out before each tile is examined or after the initial focusing such focusing can be carried out each time a predetermined number, e.g., five, of tiles has been examined.

The barcode reader 16 may be a conventional device, such as an integral barcode reader system, which is sold by Symbol Technologies, Inc of Bohemia, New York under the trademark LaserScan 6X20. Such barcode reader 16 is positioned to view a selected area of a slide once it has been transported to the stage 24 by the robotic slide handler 22. In the preferred embodiment each slide presented to the system 10 for classification must contain a barcode. The barcode contains relevant information necessary in coordinating the classification results to the slide, e.g., the doctor providing the slide and the patient from which the specimen on the slide was obtained. The barcode reader 16 reads the encoded information from the slide and provides that information to the computer system 20 via connection 80 for storage and future correlation with test (i.e., classification) results. In the event that a slide is presented to the screening system 10 without a barcode, or with an improper or unreadable barcode, the slide will be rejected and returned without classification to the cassette 23 by the robotic slide handler 22. In other embodiments the barcode and barcode reader could be replaced by a system performing similar functions, such as a set of characters and an optical character reader.

When a physician collects a cytological specimen from a patient, the physician may securely affix a barcode label (e.g., an adhesive label) to the slide on which the specimen is placed and may securely affix a corresponding label and/or barcode to the patient's chart. The chart may be retained by the physician. When the system 10 examines a slide, preferably it also prints a report of the results of such examination. The barcode information read by the system 10 preferably is printed on such report. Then the physician can compare the printed barcode information with the corresponding barcode or like information on the patient's chart to confirm accurate matching of the report to the patient. The physician also can supply the laboratory, which is using the system 10 to classify the cytological specimen, written information, such as the patient's name and the physician's name, that can be correlated with the barcode and printed automatically on the report concerning the classification specimen.

The camera 14 is positioned in the microscope's optical path 29 to capture a focused, magnified electronic image of the area of the slide being viewed. The camera 14 feeds the electronic image to the computer system 20 via a connection 81 for classification of the cells appearing in the imaged area. The camera may be a conventional three chip charge coupled RGB camera, such as one made by Sony, or other camera able to provide suitable information of the specimen, i.e., an image, to the computer. Such image is preferably represented by electrical signals which can be processed by the image processor 20b of the computer system 20.

In the computer system 20 a number of image processing and evaluation functions are performed. These include determining where on a slide is there specimen material actually located, whether there is adequate specimen material to perform a meaningful classification, and the primary classification which does a low level filtration or screening, e.g., based on morphology that can be evaluated algorithmically. The neurocomputor portion 82 of the computer system 20 provides the secondary classification, doing a higher level filtration or screening based upon training of the neurocomputer, e.g., as is disclosed in the parent patent application mentioned above and the references mentioned above as well as according to the description presented herein. Electronic image representations of cells which are classified by the primary and secondary classifiers as being suspect are stored in the computer memory, in disk memory, or in some other mass storage device for further (tertiary) classification by a person trained to detect the truly abnormal cells. The locations of such suspect cells on the slide also are stored in the computer. Subsequently, when the tertiary classifier (technician) can review the images of such suspect cells, they can be inspected or examined by viewing such stored images on a video monitor; and the technician can make a final determination as to whether each of such suspect cells is truly abnormal, e.g., malignant or pre-malignant or otherwise of interest.

When the tertiary classifier finds such an abnormal cell, she or he may use a mouse or some other device coupled to the computer 20a to point to such cell. Such cell then is identified or is tagged (e.g., in software or an electronic data representation of such cell) for convenient recall and redisplay for viewing and examination by a supervisor, pathologist, etc. An image of such cell may be printed onto paper. Also, the physical location of such cell on the slide can be marked, e.g., by placing an ink dot proximate such cell on the slide or on the cover slip thereof.

More particularly, after the tertiary classifier has identified the truly abnormal cells, the computer system 20 commands the motor control 35 and stage motors 33, 34 to position the respective areas of the slide having an abnormal cell under the slide marker 18. (If the slide had been returned to the cassette 23, the robot handler 22 first replaces the slide back on the bridge in the same position as it had been before when inspected by the camera and so on.) The slide marker 18 then is controlled by the computer 20 to make a small dot, approximately 0.25 mm in diameter, on the slide in the (several) area(s) of the slide where such abnormal cell(s) is (are) located by operation of a solenoid (not shown) to dab ink via an arm 18a onto the slide. Such marking is similar to the manner in which silicon wafers are marked for specified purposes in the field of such wafer manufacturing and inspection. The computer system 20 will then command the robotic slide handler 22 to return the classified slide to the cassette 23. Another slide then can be marked as described until all slides in the cassette have been screened. The slide marker may be one of the type sold by Xandex.

Motion of the stage 24 to bring portions of a slide S that is held on the bridge 25 is under control of the computer 20. The computer sends control signals to the interface control circuit 35, which in turn sends appropriate signals to driver circuits associated with the stepper motors 33, 34 to move the stage in the X and Y directions indicated in FIG. 1. Limit switches 90, 91, 92, 93 detect maximum travel of the stage and are coupled to the computer 20 to limit travel beyond maximum limits, as is conventional. Feedback to indicate the actual location of the stage or the relative location compared to a reference location is obtained by the position encoder 44, as is conventional.

The actual travel path of the stage to move the slide to desired locations relative to the optical path 29 and/or to move the slide to a position convenient for pick up and placement by the robot handler 22 can be programmed into the computer using conventional techniques. The moving of the stage 24, bridge 25 and slide S relative to the optical path 29 to place specific cells into the optical path for viewing during respective low and high resolution examinations by the respective objectives 30, 31 and when specific cells are desired to be reexamined also can be controlled automatically as a function of location information that can be stored in the computer and/or mass storage memory. Further, the locations to move cells for automatic dotting by the marker 18 and arm 18a also can be controlled automatically based on stored location information that is delivered to the computer 20. Appropriate offsets may be added to location information, e.g., to move a cell desired for marking relative to the marker arm 18a taking into consideration the location of the marker arm 18a, the location of the optical path, and the desire to place the mark adjacent the cell (and not directly on the cell so as to obscure the cell in case it is to be viewed subsequently).

Considering, now, the robotic slide handler 22, such device is similar to a silicon wafer robotic handler used in the semiconductor industry for automatically handling, moving, etc., silicon wafers on which integrated circuits or the like are formed. Accordingly, such handler 22 includes an arm 100, which is mounted relative to the microscope frame 40 for movement to move slides from the cassette 23 to the stage 25 and vice versa. Motive means 101 for mounting and moving such arm are provided in a support housing 102. Appropriate joints, etc., may be provided in the arm 100, depending on the degrees of freedom of movement desired. At the end of the arm 100 is a support foot 103 on which a slide actually is carried.

The foot 103 includes a top surface 104 that can fit beneath a slide S, which is shown in the cassette. An opening 105 in the surface 104 of the foot and a passage to such opening provides a source of vacuum to hold the slide S to the foot. The vacuum opening is coupled via a passage 106 and valve 107 to a vacuum source 110. Such vacuum source 110 also is coupled via vacuum line 111 and valve 112 to the vacuum lines and openings 26 in the stage 25.

The cassette 23 is mounted on an elevator 113 and preferably is held thereon by a vacuum drawn through openings 114, vacuum line 115 and valve 116. The valve 116 preferably is manually controlled (energized or deenergized) by a manually operated electrical switch 117. Closure of such switch 117 energizes the valve 116 to provide a vacuum that holds the cassette onto the elevator 113; opening of the switch deenergizes the valve to release the cassette from the the elevator enabling easy removal therefrom.

The elevator 113 includes a lift mechanism 120 and a support platform 121. An electronic control circuit 122, which can be controlled by the computer 20, provides information to the control circuit 122 to identify from where to obtain the next slide (e.g., from the cassette and where from the cassette or from the stage 25) and to where to move the slide. The control circuit 122 may be of the conventional type used in robot systems that handle silicon wafers, as was mentioned earlier. Thus, for example, upon sending the appropriate signal to the control circuit 122, the computer can initiate an operational cycle of the handler 22, say to remove a slide from the cassette 23 and to place the slide on the stage 25, and vice versa.

Coordinated operation of the arm 100, foot 103, elevator 113, stage 24, and control circuit 122 is controlled by the computer 20. As one example, to pick up a slide S from one particular location of many slide storage locations in the cassette 23, the elevator 13 lifts the cassette 23 slightly to provide clearance for the foot 103 beneath the particular slide S. The motive mechanism 101 moves the robot arm 100 and foot 103 to place the foot beneath the slide. The valve 107 then is energized by the control circuit to supply vacuum to the opening 105. Then the elevator 113 lowers the cassette 23 to lower the slide S onto the top surface 104 of the foot 103. The slide then is held onto such surface 104 by the vacuum and by gravity.

The computer by now has caused the stage 24 to move the bridge 25 to slide loading position. The arm 100 then swings to move the slide S into alignment above the openings 26 at an appropriate location on the bridge 25. The bridge 25 and/or the foot 103 are moved vertically relative to each other so that the slide is placed onto the top surface of the bridge 25. The foot 103 fits in a recess 27 in the bridge. The valve 112 is energized to supply vacuum to the openings 26 to hold the slide on the stage, and the valve 107 is deenergized to release the vacuum holding the slide to the foot.

Similar operation can be used to move the slide from the bridge 25 back to the cassette, and so on.

Figure 2:
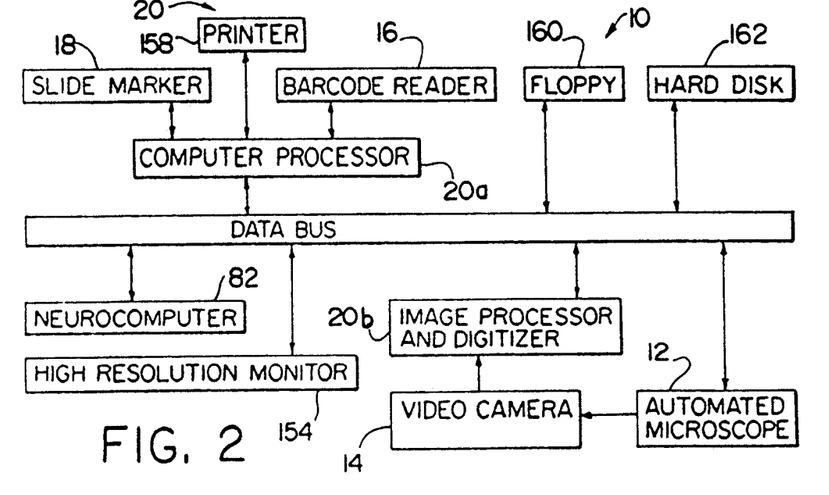
FIG. 2 is a block diagram of an automated cytological specimen screening device in accordance with the present invention with particular emphasis, on classification components.

Referring to FIG. 2, the screening device 10 is shown with particular emphasis on the classification elements embodied in the computer system 20. The computer system 20 includes an image processor and digitizer 20b, a neurocomputer 82, an output monitor 154, and a general processor 20a with peripherals for printing, storage, etc.

The general processor 20a is preferably an IBM PC/AT or compatible although it may be another computer-type device suitable for efficient execution of the functions described herein. The processor 20a controls the functioning and the flow of data between components of the device 10, causes execution of primary feature extraction algorithms such as an integrated optical density function which mainly is carried out in the image processor 20b, and handles the storage of image and classification information. The processor 20a additionally controls peripheral devices such as a printer 158, floppy and hard disk storage devices 160, 162, and the barcode reader 16, slide marker 18, autofocus 46, robotic slide handler 22, stage motor controller 35, and objective carriage 45 components described more fully above.

The image processor and digitizer 20b also performs primary cell classification functions such as thresholding and erosion and dilation. In the preferred embodiment, the image processor and digitizer 20b is a commercially available low level morphological feature extraction image classifier such as the ASPEX Incorporated PIPE (TM) image processor which includes an image digitization function. Alternatively, the image processing and digitization function could be separated into two or more components.

Secondary group processing cell classification is performed by the neurocomputer 82. The neurocomputer 82 is a computer embodiment of a neural network trained to identify suspect cells. In this embodiment the parallel structure of a three-layer back propagation neural network is emulated with pipelined serial processing techniques executed on one of a host of commercially available neurocomputer accelerator boards. The operation of these neurocomputers is discussed in the Spectrum reference cited. The neural network is preferably implemented on an Anza Plus processor, which is a commercially available neurocomputer of Science Hecht-Nielsen Neurocomputers (HNC) (see the Hecht-Nielsen reference above). Alternatively, secondary cell classification functions could be performed using a template matching algorithm designed to identify shapes known to be typical of a pathological cell. A template matching or other group processing algorithm could be efficiently implemented in a parallel distributed processing network, for example. Another alternative secondary classification embodiment is a holographic image processor designed to perform group based classification.

Figure 3A:
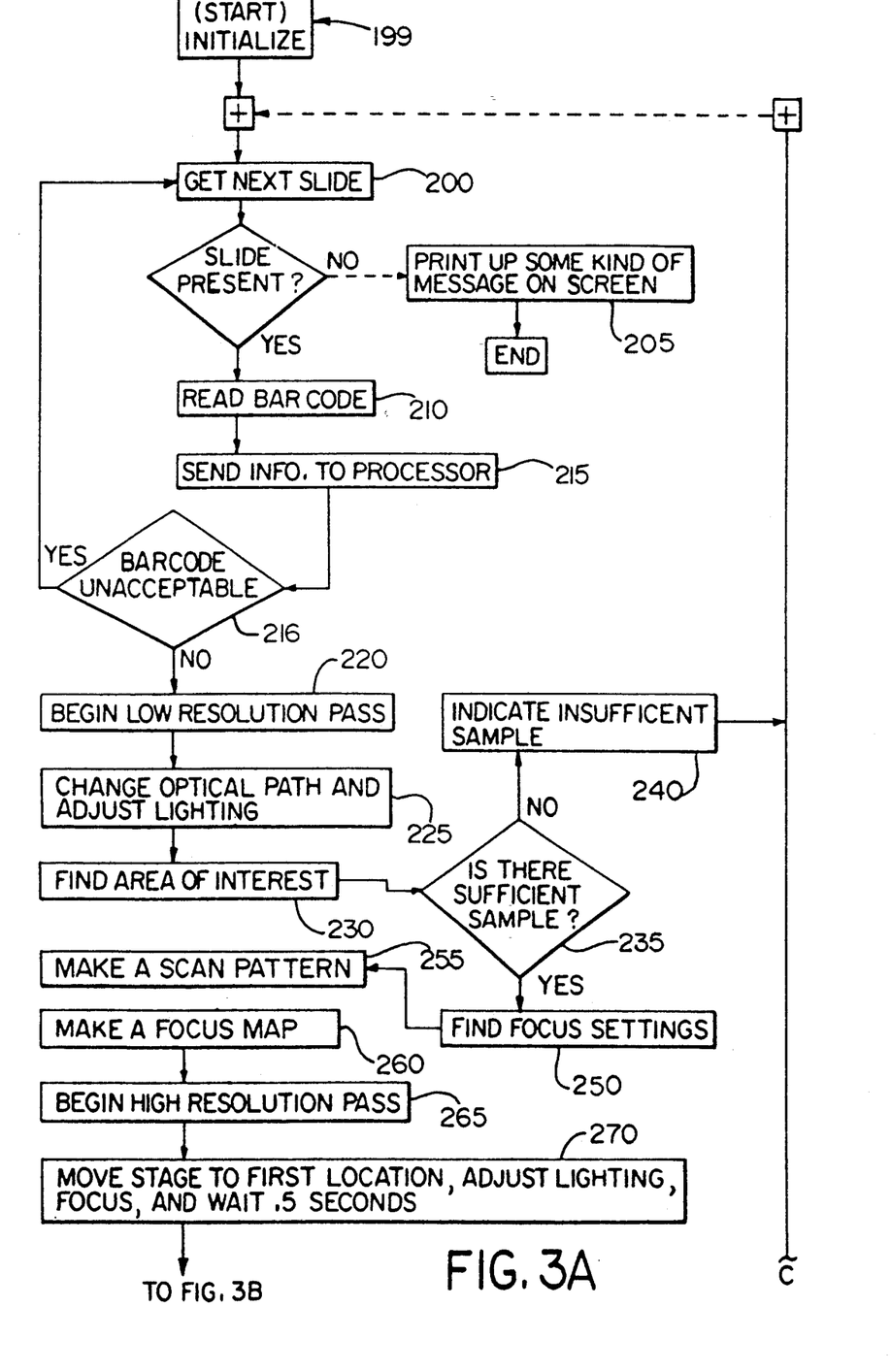
FIGS. 3A through 3C present a schematic flow chart short-hand representation of the method of classifying objects in an exemplary operation of the invention.
Figure 3B:
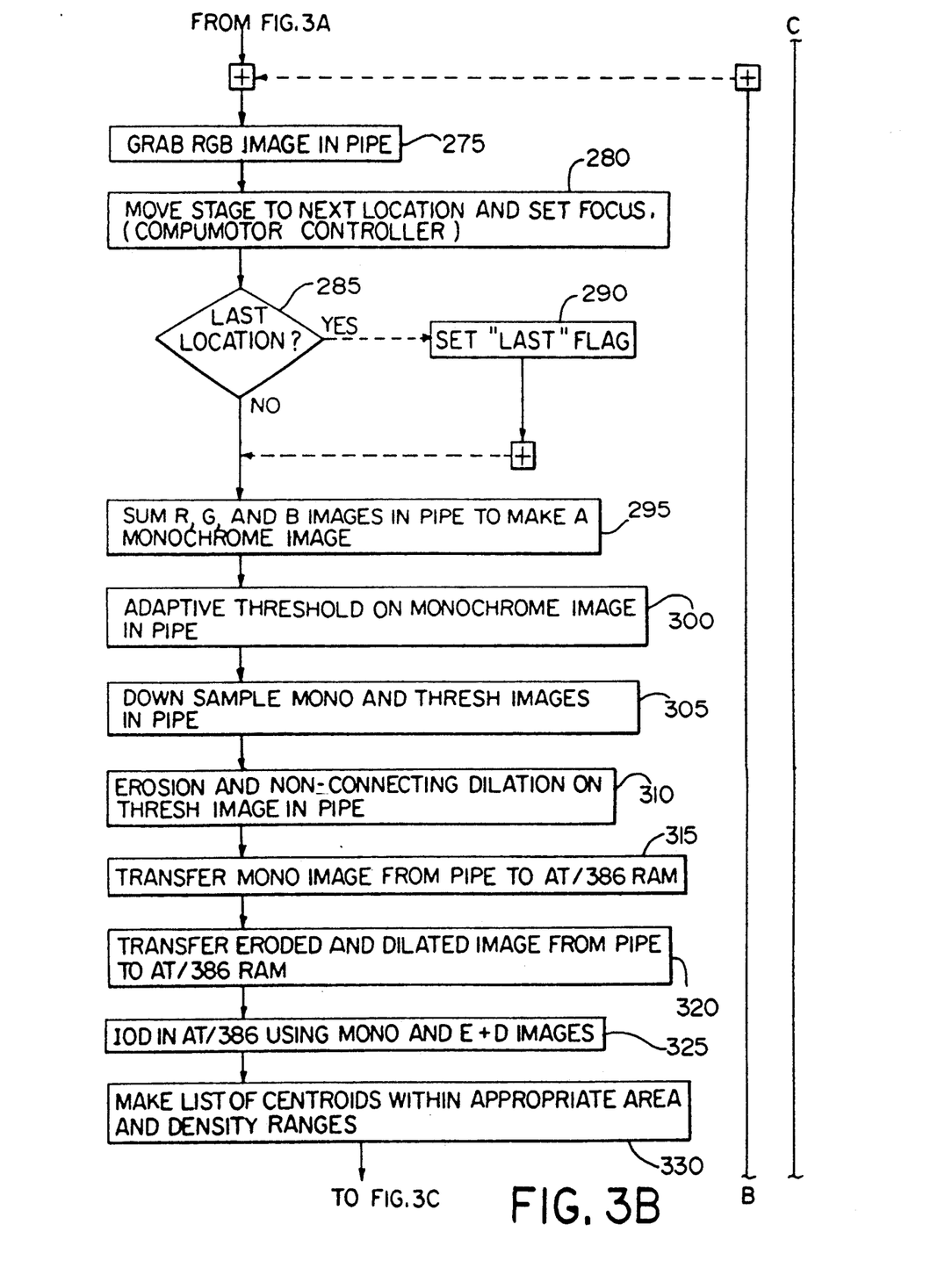
Figure 3C:
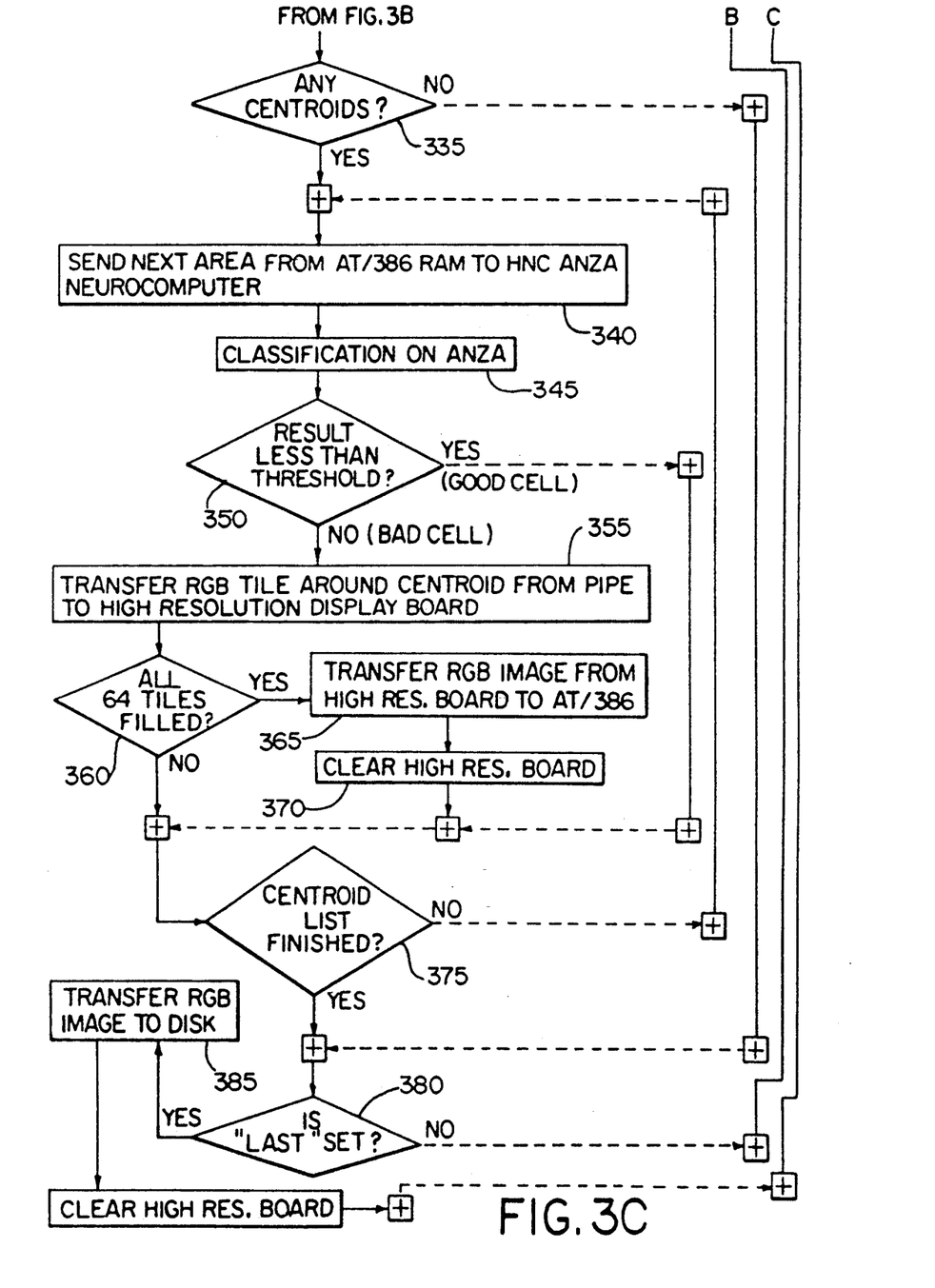

Referring to FIGS. 3A through 3C a flow diagram of the operation of the cell classification method of the present invention is outlined Initialization of the system 10 is carried out at block 199. During initialization the image processor 20b is initialized so as to be ready to receive the first electronic information representing the image received by the camera 14 and to process the image information. Also the stage 24 is initialized to place it in a reference location, sometimes referred to as a home location so that the computer 20 can expect to know that the stage is at such location and can determine future locations based on the home location. The robot handler 22 is initialized, too, to place the various portions thereof in a home position to so that future locations and movements thereof can be determined from the initial home position. The neural net also is initialized in conventional fashion.

To begin operation, the robotic slide handler 22 grabs the first slide from the cassette 23 and transports it to the motorized stage 24 (block 200). If the robotic slide handler was unable to find the next slide, such as when all slides in the cassette 23 have been classified, a message is conveyed to the operator (205). Assuming a slide is present, the barcode reader 16 reads the barcode information from the slide (210) and passes the information to general processor 20a (215) for correlation with future classification data. Cells not having barcodes or barcodes that are not readable are rejected and the next slide is processed (216). Next, the general processor 20a commands the stage motor controller 35 and motors 33, 34 to move the stage 24 and slide into the optical path 29 of the microscope system 12 for the low resolution pass (220).

In the low resolution pass, the carriage 45 will move the low resolution objective 30 into the optical path 29, and the autoiris 51 will automatically adjust the lighting for the low resolution objective (225). A relatively quick scan of the slide is then made to find the areas of the slide having cellular matter (230). If the no areas having cellular matter or an adequate amount of matter for valid classification is found on the slide, then the slide is identified as containing insufficient cellular matter to perform a meaningful test (235); the slide then may be rejected (240) and screening of the next slide may begin (200).

To determine whether there is adequate cellular material on the slide or at various locations on the slide and also to determine the focus map for the slide, the following may be carried out by the computer system 20. First, a scan route is determined so that a plurality of areas on the slide can be viewed sequentially. Such areas may be located in a straight line along the length of the slide S or in some other arrangement on the slide. As an example, a plurality of areas sequentially located along a serpentine path along the slide are viewed. Each such area will be designated hereinafter a "macro-tile".

When a particular macro-tile is located in the optical path 29, the camera 14 takes a picture thereof. The macro-tile may be, for example, 2 mm by 2 mm in size. In the image processor 20b, using an ISMAP program or algorithm available from ASPEX Incorporated, New York, N.Y., (iconic to symbollic mapper) the macro-tile is subdivided into sixteen areas referred to below as "tiles" and a sharpness image and a gray scale image are made. These images are used to determine whether there is and/or how much there is of cellular material in the macro-tile. A histogram of the absolute value of the difference between such images may be used in the focus function of the computer 20 to determine a focus map for the slide.

More particularly, the value of the optical transmission characteristics of the macro-tile is made; and simultaneously two successive 3 by 3 Gausian filtrations are made to provide a 5 by 5 Gausian result. The difference between the two is taken and is converted to absolute value, which represents a sharpness image that can be used for the focus map.

In other words, a sharpness image is obtained for the macro-tile; and a synthetically created gray scale map that is the size of the macro-tile is made. The gray scale map has multiple areas that correspond to the respective tiles of the macro-tile. The incremental gray scale is determined according to the values in the sharpness image using histogram techniques.

If any of the bins in the histogram (which represent respective tiles in the macro-tile) is above a threshold value, then the particular tile is noted for high resolution examination and processing because there appears to be adequate cellular material there. Furthermore, by taking a further histogram of the absolute value of the difference between the original transission characteristic of the macro-tile and the gray scale Gaussian filtered image, one can determine the particular maximum for the tile; and such maximum may be used as a representation of the optimum focus condition for the automated microscope for viewing the particular tile during the high resolution pass. See block (250) in FIG. 3.

The advantage of determining whether there is adequate sample on the slide for classification during the low resolution pass in the microscope 12 is that such determination can be made relatively quickly compared with the time needed to make the same determination using the high resolution objective 31. The advantage of determining, during the low resolution pass, which tiles will require further examination in the high resolution pass, is to save the time needed unnecessarily to examine tiles that do not have cellular material or adequate cellular material there.

The scan pattern of the areas (tiles) of interest is made (255) and focal information for each tile is correlated with position coordinate information for that tile from the position encoder 44 to provide a focus map (260).

All information necessary to perform a high resolution scan of the slide is now available. To commence the high resolution pass in the microscope 12, the computer 20 operates the motor 53 to move the carriage 45 to place the high resolution objective 31 into the microscope's optical path 29 (265). The lighting is automatically adjusted by the autoiris 52 and motor 60 for the high resolution objective, and the stage 24 is moved to bring the first tile or segment of the slide S intended to be examined into the viewing field of the objective 31. The computer 20a commands the autofocus 46 to adjust focus for the area, segment or tile (270) of the specimen under examination by providing an appropriate offset signal on line 79 to the differential amplifier 77.

The camera 14 obtains a color video picture of the focused image (275, FIG. 3B), and that image is digitized and is stored (sometimes referred to as frame grabbing), as is described further herein. The stage 24 then moves the next tile or segment into view and appropriate focal adjustments are made in accordance with the focus map (280). If the last segment (tile) of the slide has been reached (285), a flag is set and processing of the slide will be discontinued after screening of that segment (290). The stage 24 may wait at a location until an image of a tile is obtained. Preferably, though, such waiting time should be minimized to minimize the time needed to examine a slide.

Preferably image processing of one or more than one segment or tile can be carried out in the image processor 20b simultaneously while an image of another segment is being obtained by the camera 14.

The color components of the video representation of a segment are summed to provide a monochrome image (295), and that image is passed to the image processor and digitizer 20b where the primary classification of the segment begins. Initially, the image processor and digitizer 20b performs an adaptive threshold operation on the video image to enhance the image contrast and eliminate noise from the background (300). This thresholded image is then down sampled to a manageable digital representation (305). The image processor and digitizer 20b can then perform erosion and non-connecting dilation operations on the digital image to separate the objects in the segment (310). The monochrome and resultant filtered images are transferred to RAM of the general processor 20a (315, 320).

The erosion and dilation techniques are conventional image processing techniques. They eliminate the effect of overlapping cells in which dark areas on may appear due to the increased density of the overlap rather than due to enlarged or especially dark cell nucleii. It is usually the darkened nucleii or large size nucleii that are detected during the integrated optical density (IOD) evaluation made in the low level classification procedure described further below. The erosion and dilation technique also enhances the accurate examination of the cells during the low level classification.

The processor 20a then performs further primary feature extraction classification on the segment such as with an integrated optical density (IOD) algorithm (325). Other morphological algorithms may alternatively or additionally be used to classify based on features, such as color or features relating to DNA ploidyanalysis, immuno histochemistry, DNA hybridization, etc. These feature extraction algorithms isolate certain objects which possess features typically known to be present in pathologic cells, such as a dark cell nucleus which is abnormally large in relation to the rest of the cell. The centroids of objects identified by primary classification as being possibly pathological are catalogued and stored in RAM of the processor 20a (330). If no objects have been identified (335, FIG. 3C), classification begins on the next segment (295).

Identified objects, i.e., electronic image representations of those which have not been eliminated by the low level classification, are transferred individually to the neurocomputer 82 as digital areas around the object centroid (340). The neurocomputer 82 will perform secondary classification on the objects in accordance with its previously completed training which is described more fully below (345). Additionally, the neurocomputer 82 may also determine if it has received a sufficient number of cells from the primary classifier to indicate a valid test. For objects identified by the neurocomputer 82 as suspect (350), the color representation of a suitable area surrounding the centroid is retrieved from disk and transferred to the high resolution display board of the high resolution monitor (355). Cells having a classification less than the threshold level are discarded and the next centroid is obtained from the general processor (340) and classified (345). When it is determined that all locations, tiles, on the display board are occupied (360), the total image is transferred to the general computer 20a for temporary storage (365) until all cells on the slide have been screened, and the high resolution board is cleared (370). Once all centroids found in the primary classifier for that segment have been classified by the neurocomputer (375), the image for another segment is grabbed (275), and classification for that segment is performed (295-375).

When all segments on a slide have been screened (380), the high resolution color images for the slide are transferred to disk (385) for storage until a convenient time for display on the high resolution monitor and tertiary classification by a cytotechnician or cytologist. All arrays of suspect cells may be tagged in memory with information obtained from the barcode to identify the slide on which they were found. The location of the suspect cells on the slide also may be physically marked on the slide by the slide marker 18. A report indicating the test results for that slide, which is correlated with the barcode information obtained from that slide, may be printed on the printer 158 now or later.

The slide is then returned to the cassette 23, and another slide is selected (200) to begin the classification process anew.

It should be recognized that while the image processor and digitizer 20b, the general processor 20a, and the neurocomputer 82 are described and shown in FIGS. 3A through 3C operating in a serial manner, in actual practice as many functions will be performed in parallel as is possible. Consequently, the components 20b, 82, 20a may process different slide segments or different areas of a segment concurrently, greatly reducing the time required to screen a slide.

Figure 4:
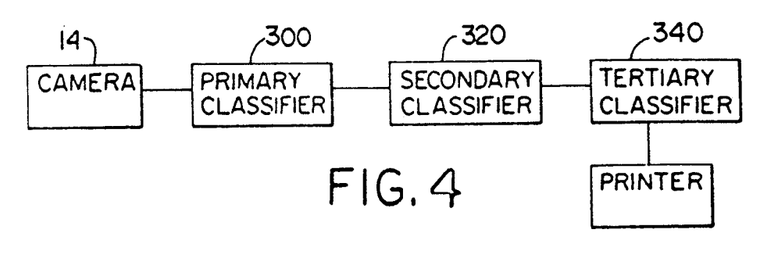
FIG. 4 is a block diagram representation of the method of cell classification used by the device of FIG. 1.

Turning to a more in-depth review of the classification method and with reference to FIG. 4, a block representation of the classification functions of the screening device 10 is illustrated. Primary classification, such as low level morphological feature extraction, is performed as indicated above by both the image processor and digitizer 20b and general processor 20a and is represented in FIG. 4 conjunctively as block 400.

Initially, as described more fully above, the video camera 14 obtains an image of the cytological specimen which is digitized for classification use. The primary classifier 400 first performs an erosion of the image. This erosion operation successively peels off layers of pixels from each object in the image so that all of the objects which are smaller in size than the smallest known pathological cell nucleus are removed from the image. The remaining objects are then dilated, i.e., regrown, by successively adding back layers of pixels to these objects, but they are not dilated to the point where they are touching each other. The basic operations of erosion and dilation can be found in several sources in the prior art (e.g., Serra, J., "Image Analysis and Mathematical Morphology", Academic Press, 1982).

Based on experience with an engineering prototype, it has been found that for every 1,000 objects found in a typical benign Pap smear no more than about 15 objects will pass the erosion/dilation screen. These relatively few remaining objects are then subjected by the primary classifier 25 to an integrated optical density (IOD) screen.

Integrated optical density is the sum of the pixel grey values for each object. Pre-malignant cells tend to possess large dark nuclei. The IOD threshold is, therefore, set to filter out any object which passes the erosion/dilation screen but which has an IOD which is above or below the threshold displayed by a truly pre-malignant or malignant cell. For the 15 objects which passed the erosion/dilation screen, experience shows that no more than ten objects will pass the IOD filter. Thus, the average combined filtration of erosion/dilation and IOD reduces an input image of 1,000 objects to an output image of ten objects. These ten objects may include not only pre-malignant and malignant cells but also other objects with a high integrated optical density such as cell clumps, debris, clumps of leucocytes and mucus. The task of the secondary classifier 420 is to distinguish the pre-malignant and malignant cells from these other objects.

For the engineering prototype, classifier 420 was a back propagation neural network hosted on an Anza Plus neurocomputer coprocessor board resident on an IBM PC. The back propagation network was trained with a training set of several hundred known benign and pre-malignant or malignant cells to associate a benign image with a diagnosis of 0.1 and a non-benign image with a diagnosis of 0.9.

In actual operation, the secondary classifier 420 is presented with images passed to it by primary classifier 400. These are images which may be similar but are not identical to those used to train classifier 420. The task for secondary classifier 420 is thus to generalize from its training process to successfully classify benign and non-benign images to which it was not previously exposed.

One major advantage of the present invention over the prior art resides in the fact that each image presented to the secondary classifier 420 is pre-centered by the primary classifier 400 on the centroid of the suspect cell nucleus. This is accomplished because erosion/dilation and IOD based filtration automatically results in a centering of each suspect image around its dark centroid. In prior art attempts to utilize neural networks and other high-level template matching pattern classifiers for image recognition, difficulty has been encountered in consistently presenting the classifier with the centroid of the image requiring classification. To use an example from another application domain, back propagation networks are excellent at reading handwritten zip code digits but have difficulty in finding where the zip code is on the envelope. The present invention overcomes this difficulty in the domain of cytology.

In an engineering prototype, a 128×128 pixel image was stored around each centroid which passed the low level filters of classifier 400. A 64×64 window, also centered around the same centroid, was then compressed using pixel averaging to a 24×24 pixel image. Note that this image is still centered on the same large, dark, image which passed the erosion/dilation and IOD filters of classifier 400. A set of several hundred of these precentered 24×24 pixel images of known benign and non-benign cells was used to train classifier 420. During feed-forward, i.e., post-training operation, when classifier 420 is presented with new images it did not encounter during its training it must generalize from the training set images to select the diagnostic category which most closely matches the new image. A fundamental advantage of the present invention over the prior art is that during this feed-forward, post-training phase of its operation, classifier 320 is presented with precisely the same type of 24×24 pixel images on which it was trained. These images are also centered on the centroid of the suspect nucleus by classifier 400 in a manner identical to that used to prepare the training set images. This makes the generalization task of classifier 420 far easier and thus much more successful than anything found in the prior art.

As noted above, classifier 420 is trained to associate a known benign image with an output of 0.1 and a known pathological image with an output of 0.9. Such outputs represent, for example, the degree of certainty that a cell is normal or abnormal, respectively. When classifier 420 is then presented with new, unknown cells, it generalizes from its training and attaches an output to the image. The closer that classifier 420 is able to categorize the unknown image into the benign category, the closer is its feed-forward output equal to 0.1. Conversely, the more closely that an unknown image appears to classifier 420 to resemble the non-benign images of its training set, the closer is its feed forward output for that image equal to 0.9.

During testing of an engineering prototype in which a back propagation neural network was used for classifier 420, it was found that no truly pre-malignant or malignant cell was attached to an output of less than 0.75. In order to provide a margin of safety, classifier 420 only screens out images with an output of 0.65 or less. Any image which is attached to an output greater than 0.65 is assumed to be a suspect pre-malignant or malignant cell. For each of these suspect images, the associated 128×128 pixel image centered around its centroid is retrieved from image memory and displayed as one of a field of 64 such images on a high resolution output monitor for final classification by a cytotechnologist.

All images which are classified by classifier 420 to have an output of 0.65 or less are assumed to be benign and are not displayed on the output monitor. During testing of the above-described engineering prototype, it was found that classifier 420 consistently filtered out over 80% of the benign images sent to it by the output of classifier 400. In other words, over 80% of the truly benign images which pass the erosion/dilation and IOD screens of classifier 400 are assigned an output of less than 0.65 by classifier 420, leaving 20% of these images representing suspect benign or pre-malignant and malignant cells to be finally classified by the tertiary classifier 440, i.e., the cytotechnologist.

As mentioned above, in an alternate embodiment the classifier 420 may be a high level template matching or holographic imaging filter. It is possible to use these filters in an efficient overall processing scheme because the object of interest has already been identified by the low level feature extraction filter, classifier 400.

Figure 5:
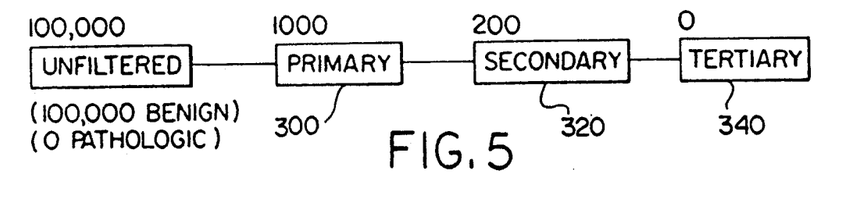
FIG. 5 is a block diagram of a classification of a slide having no pathological cells.
Figure 6:
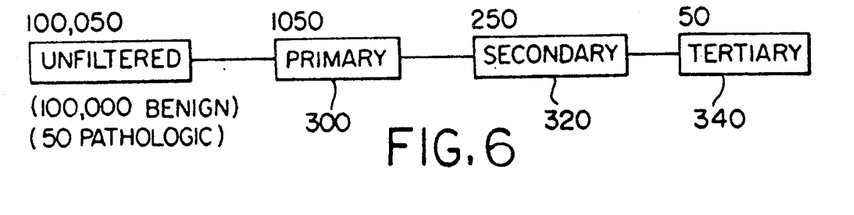
FIG. 6 is a block diagram of a classification of a slide having 50 pathological cells.

The overall operation of the cell classification system can be summarized with reference to FIGS. 5 and 6. FIG. 5 shows the screening of a typical Pap smear which contains approximately 100,000 benign cells and other objects. Through erosion/dilation and IOD filters, the primary classifier 400 will filter out 99% of these objects, passing approximately 1,000 objects to the secondary classifier 420. Classifier 420, which in the tested and preferred embodiment employs a three-layer back propagation neural network, in turn filters out 80% of these 1,000 objects, passing the images of approximately 200 residual objects deemed to be most suspect of pathology to the output monitor for tertiary human inspection 440. These 200 objects are assembled as two to three fields of 64 objects each. Each object is presented as a 128×128 pixel image taken from the video input to classifier 400 and centered around the suspect cell nucleus. The tertiary classifier 440, the cytotechnician or cytologist, will then further screen the 200 objects to zero, since all were benign.

The screening of a Pap smear having 50 pathological cells plus the approximately 100,000 cells and other objects (classified above) is shown in FIG. 6. The primary classifier 400 will screen the slide down to 1050 cells (50 pathological cells and 1000 possibly pathological cells). The secondary classifier 420 will further screen these cells to 250 cells (50 pathologic plus the 200 most suspect beneign cells). These 250 cells will then be screened by the tertiary human classifier 440 resulting in 50 cells being classified as pathological.

The overall result is that instead of examining 100,000 cells under the microscope, the cytotechnologist examines 200 to 250 cells presented on a high resolution color video screen, each screen containing 64 images, with the attention of the cytotechnologist focused on inspection of the center of each of the 64 128×128 pixel images.

Moreover, according to the invention such images may be presented to the cytotechnician one at a time, in an array of four, sixteen, or more or less images, and those images may be presented at various levels of magnification, which further facilitates and enhances accuracy of the tertiary classification.

The false negative rate of cytological screening is known to be a function of the ratio of non-pathological to pathological objects which are visually inspected on a daily, continuous basis. The present invention drastically reduces the number of non-pathological objects which require inspection from 100,000 to 200-250. In addition, all suspect cell nuclei are pointed out to the examiner by their position in the center of a 128×128 pixel rectangle. The result is a very much less fatigued cytotechnologist and a very significant reduction in the false negative rate.

As will be evident to those of ordinary skill in the art, the present invention overcomes all of the obstacles to practical automated cytological analysis inherent in the prior art. This is achieved by the present invention's unique combination of feature extraction and template matching techniques. This combination of techniques overcomes the requirement for image segmentation found in the prior art. In addition, this combination of techniques overcomes the major obstacle of neural networks and other computationally intensive template matching techniques for the analysis of complex images such as cervical smears. This is achieved by the fact that the primary classifiers of the present invention result in an automatic centering of the suspect cell nucleus in the input array of the neural network.

By simultaneously overcoming the requirement for image segmentation and also enabling the first practical utilization of neural networks for cytology, the present invention has resulted in the first practical automated cytological screening system. The present invention has been demonstrated by an engineering prototype to successfully analyze standard Pap smears with overlapping and partially obscured cells. It has also been shown to perform this analysis within the time period typically consumed by completely manual examination. Thus, the unique combination of techniques embodied in the present invention has achieved the goal of over twenty years of prior art attempts at automated cytological classification.

However, the invention is not limited to use as a primary screening device, but may also be used to rescreen cells which a cytotechnician has already inspected and classified as benign. As such, the device provides an effective check to focus the cytotechnician's attention to cells which may have been overlooked during the initial screening.

The invention can be designed and trained to classify other objects not expected to be found in a typical Pap smear. Such an object may be representative, for example, of a herpes virus.

The invention may also be used in classifying unexpected cells on a slide which has previously been screened by a cytologist or cytotechnician on another basis. One such instance is in the classification of a Pap smear taken for a post-menopausal patient. Such a smear should not contain endometrial cells. Other instances are screening for organisms, etc. Consequently, the slide will be analyzed by a cytologist for the presence of endometrial cells or other organisms and then screened by the invention for other unexpected cells or viruses, such as malignant/pre-malignant cells or the herpes virus.

Another important feature of the present invention is the ability to provide adaptive learning for the neural computer 82. Such adaptive technique enables the neural computer 82 to be retrained or to be trained with additional information representing additional or better defined cells of specified characteristics. Characteristics of such cells may be those of malignant or premalignant cells; may be those of benign cells; may be those of other types of cells or characteristics of other types of matter expected to be found in samples intended for examination and classification. Further, such adaptive training can be carried out in a laboratory or research facility and the results of such training can be delivered to apparatus employing the invention in the field.

It will also be appreciated that while the invention is described with primary reference to Pap smears, the invention is applicable to most any type of cytological specimen such as those containing exfoliative or aspirated cells, for example.

What is claimed is:

1. A cytological specimen classifier, comprising:
   a) microscope means for obtaining a view of at least part of a cytological specimen,
   b) camera means for creating an image of such view,
   c) image digitizing means for producing a digital representation of such image,
   d) a primary classifier for identification of objects in such digital representation based on a detectable feature, and
   e) secondary adaptive classifier means for recognition of cells having patterns atypical of patterns in cells expected in the specimen among the objects identified by the primary classifier.

2. The classifier of claim 1, further including tertiary classifier means for detection of atypical cells among the cells recognized by the secondary classifier.

3. The classifier of claim 2, further including a high resolution color monitor to facilitate tertiary classification of cells recognized by the secondary adaptive classifier means.

4. The classifier of claim 1, wherein said secondary adaptive classifier means includes a neural network.

5. The classifier of claim 1, further including means for reading information from a slide containing a cytological specimen.

6. The classifier of claim 5, wherein said means for reading information includes a barcode reader.

7. The classifier of claim 5, wherein said means for reading information includes an optical character reader.

8. The classifier of claim 1, further including means for marking a location of a cell recognized by the secondary adaptive classifier means on the cytogical specimen.

9. The classifier of claim 1, wherein said primary classifier includes a computer processor.

10. The classifier of claim 9, wherein said computer processor includes memory for storing digital representations of images after classification.

11. The classifier of claim 1, said secondary adaptive classifier means comprising means for recognizing cells having patterns typical of malignant or pre-malignant cells.

12. The classifier of claim 1, said secondary adaptive classifier means comprising means for recognizing cells having patterns typical of endometrial tissue.

13. The classifier of claim 1, said primary classifier comprising means for eroding and dilating objects to screen objects in such digital representation.

14. The classifier of claim 1, said primary classifier comprising means for screening objects in such digital representation on the basis of the color of the objects.

15. The classifier of claim 1, wherein said secondary adaptive classifier means includes a parallel processor.

16. The automated classifier of claim 1, said microscope means comprising an automated microscope.

17. The automated classifier of claim 1, said camera means comprising a video camera.

18. The automated classifier of claim 1, said camera means comprising a charge coupled device.

19. The automated classifier of claim 1, said primary classifier comprising a primary statistical classifier.

20. The automated classifier of claim 1, said primary classifier comprising means for detection of objects in such digital representation which have a feature that exceeds a threshold level.

21. The automated classifier of claim 1, said primary classifier comprising means for detection of objects in such digital representation which have a feature that exceeds a threshold integrated optical density.

22. The automated classifier of claim 1, said primary classifier comprising means for detection of objects in such digital representation of a cytological specimen based on morphological criteria.

23. A quality control cytological specimen classifier for classifying specimens which previously have been screened as not containing pre-malignant or malignant cells, comprising:
   a) microscope means for obtaining a view of a prescreened cytological specimen,
   b) camera means for creating an image of such view,
   c) image digitizing means for producing a digital representation of such image,
   d) a primary classifier for identification of objects in such digital representation of a cytological specimen based on a detectable feature,
   e) secondary adaptive classifier means for recognition of cells having patterns typical of pre-malignant or malignant cells among the prescreened objects identified by the primary classifier, and
   f) a tertiary classifier for detection of malignant and pre-malignant cells among the prescreened cells recognized by the secondary classifier.

24. A method of classifying objects in a cytological specimen, comprising the steps of:
   a) obtaining a view of a cytological specimen,
   b) creating an image of such view,
   c) producing a digital representation of such image,
   d) primarily classifying objects in such digital representation of a cytological specimen based on a detectable feature, and
   e) secondarily classifying cells having features atypical of cells expected in the specimen among the objects identified in the primary classification step using adaptive processing.

25. The method of claim 24, further including the step of tertiarily classifying cells recognized by the secondary classification step for detection of unexpected cells.

26. The method of claim 24, wherein said adaptive processing includes performing classification by a neural network.

27. The method of claim 24, further including the step of marking a location of a cell recognized by the secondary classification step.

* * * * *

REEXAMINATION CERTIFICATE (2979th)
United States Patent [19]
Rutenberg et al.

[11] B1 5,287,272
[45] Certificate Issued Aug. 27, 1996

[54] AUTOMATED CYTOLOGICAL SPECIMEN CLASSIFICATION SYSTEM AND METHOD

[75] Inventors: Mark R. Rutenberg, Monsey, N.Y.; Thomas L. Hall, Pasadena, Calif.; Robert Domes, Newbury Park, Calif.; Richard Chaban, Ventura, Calif.; Thomas Dulak, Newhall, Calif.; James M. Herriman; John Porzio, both of New York, N.Y.; Randall L. Luck, Brooklyn, N.Y.; James Knapp, New York, N.Y.

[73] Assignee: Neuromedical Systems, Inc., Monsey, N.Y.

Reexamination Request:
No. 90/003,817, May 1, 1995

Reexamination Certificate for:
| | |
|---|---|
| Patent No.: | 5,287,272 |
| Issued: | Feb. 15, 1994 |
| Appl. No.: | 420,105 |
| Filed: | Oct. 11, 1989 |

Related U.S. Application Data

[63] Continuation-in-part of Ser. No. 179,060, Apr. 8, 1988, Pat. No. 4,965,725.

[51] Int. Cl.⁶ .............................. G06F 15/18; G06K 9/62
[52] U.S. Cl. .................... 364/413.01; 382/133; 382/156; 382/159

[56] References Cited

U.S. PATENT DOCUMENTS

| | | |
|---|---|---|
| 3,315,229 | 4/1967 | Smithline . |
| 3,699,336 | 10/1972 | Ehrlich et al. . |
| 3,824,393 | 7/1974 | Brain . |
| 4,045,655 | 8/1977 | Suzuki et al. . |
| 4,129,854 | 12/1978 | Suzuki et al. . |
| 4,213,036 | 7/1980 | Kopp et al. . |

OTHER PUBLICATIONS

Reinhardt et al., "Structure Analysis and Classification of Cervical Cells Using a Processing System Based on TV", *Analytical and Quantitative Cytology,* vol. 1, No. 2, pp. 143-150 (The International Academy of Cytology Jul.-Aug. 1979).

Bacus et al., "Optical Microscope System for Standardized Cell Measurements and Analyses", *Applied Optics,* vol. 26, No. 16, pp. 3280-3293 (Optical Society of America 15 Aug. 1987).

Bartels et al., "High Resolution Prescreening Systems For Cervical Cancer", *Proceedings of the International Conference on Automation of Uterine Cancer Cytology,* pp. 144-184 (Tutorials of Cytology, Chicago, Illinois 1976).

Green, "A Practical Application of Computer Pattern Recognition Research: The Abbott ADC-500 Differential Classifier", *The Journal of Histochemistry and Cytochemistry,* vol. 27, No. 1, pp. 160-173 (The Histochemistry Society, Inc. 1979).

Tanaka et al., "Automated Cytologic Screening System (CYBEST Model 4): an Integrated Image Cytometry System", *Applied Optics,* vol. 26, No. 16, pp. 3301-3307 (The Optical Society of America, 15 Aug. 1987).

Tanaka et al., "CYBEST Model 4 Automated Cytologic Screening System for Uterine Cancer Utilizing Image Analysis Processing", *Analytical and Quantitative Cytology,* vol. 9, No. 5, pp. 449-454 (The International Academy of Cytology Oct. 1987).

Abmayr et al., Progress Report of the TUDAB Project for Automated Cancer Cell Detection, *The Journal of Histochemistry and Cytochemistry,* vol. 27, No. 1, pp. 604-612 (The Histochemical Society, Inc. 1979).

(List continued on next page.)

*Primary Examiner*—Ruth S. Smith

[57] ABSTRACT

An automated screening system and method for cytological specimen classification in which a neural network is utilized in performance of the classification function. Also included is an automated microscope and associated image processing circuitry.

OTHER PUBLICATIONS

Tucker, Automatic Screening of Cervical Smears, *Machine Perception of Patterns and Pictures*, pp. 88–96, (Proceedings of the Conference Organized by the Physics in Industry Subcommittee of the Institute of Physics in collaboration with The National Physical Laboratory and the Institution of Electrical Engineers held at The National Physical Laboratory, Teddington, Middlesex, 12–14 Apr. 1972).

Pycock et al., Use of the MAGISCAN Image Analyser in Automated Uterine Cancer Cytology, *Analytical and Quantitative Cytology*, vol. 2, No. 3, pp. 195–202 (The International Academy of Cytology Sep. 1980).

Erhardt et al., "FAZYTAN–A System for Fast Automated Cell Segmentation, Cell Image Analysis and Feature Extraction Based on TV–Image Pickup and Parallel Processing", *Analytical and Quantitative Cytology*, vol. 2, No. 1, pp. 25–40 (The International Academy of Cytology Mar.–Apr., 1980, presented at the 1979 International Conference on Pattern Recognition of Cell Images, Chicago, IL, May 21–23, 1979).

Swank et al., "Optical Automation For Sputum Cytology", *Applied Optics*, vol. 26, No. 16, pp. 3373–3378 (Optical Society of America 15 Aug. 1977).

Peet et al., "A Computer–Assisted Cell Identification System", *Analytical and Quantitative Cytology*, vol. 6, No. 1, pp. 59–70 (The International Academy of Cytology Mar. 1984).

Bengtsson, "The Measuring of Cell Features", *Analytical and Quantitative Cytology and Histology*, vol. 9, No. 3, pp. 212–217 (The International Academy of Cytology Jun. 1987).

Dayhoff et al., "Neural Networks for Medical Image Processing: A Study of Feature Identification", pp. 271–275, (SCAMC, Inc. Nov. 1988).

Publication entitled "The Second International Conference on Artificial Intelligence Systems (Expert Systems) as Diagnostic Consultants for the Cytologic and Histologic Diagnosis of Cancer", *Abstracts*, (The International Academy of Cytology, American Society of Cytology, The Tutorials of Cytology at the University of Chicago, Mar. 13–15, 1988) (Held at the Drake Hotel Chicago Il).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-27 is confirmed.

New claims 28-41 are added and determined to be patentable.

1. A cytological specimen classifier, comprising:
   a) microscope means for obtaining a view of at least part of a cytological specimen,
   b) camera means for creating an image of such view,
   c) image digitizing means for producing a digital representation of such image,
   d) a primary classifier for identification of objects in such digital representation based on a detectable feature, and
   e) secondary adaptive classifier means for recognition of cells having patterns atypical of patterns in cells expected in the specimen among the objects identified by the primary classifier.

28. *The classifier of claim 1, wherein said patterns atypical of patterns in cells expected in the specimen include patterns typical of cells infected by virus.*

29. *The classifier of claim 1, wherein said secondary classifier means includes means for recognition of cells having patterns atypical of patterns in cells expected in a normal specimen.*

30. *The classifier of claim 29, wherein said cells having patterns atypical of cells expected in a normal specimen include premalignant cells.*

31. *The classifier of claim 29, wherein said cells having patterns atypical of cells expected in a normal specimen include malignant cells.*

32. *The classifier of claim 1, wherein said secondary adaptive classifier means includes a non-algorithmic classifier.*

33. *The classifier of claim 1, wherein said detectable feature includes a feature typically found in a premalignant or malignant cell.*

34. *A cytological specimen classifier, comprising:*
   *a) microscope means for obtaining a view of at least part of a cytological specimen,*
   *b) camera means for creating an image of such view,*
   *c) image digitizing means for producing a digital representation of such image,*
   *d) a primary algorithmic classifier for identification of objects in such digital representation based on the likli-hood that an object is a premalignant or malignant cell, and*
   *e) secondary adaptive classifier means for recognition of cells having patterns typical of premalignant or malignant cells among the objects identified by the primary classifier.*

35. *The classifier of claim 34, wherein said secondary adaptive classifier means includes a non-algorithmic classifier.*

36. *The classifier of claim 34, wherein said secondary adaptive classifier means includes a neural network based classifier.*

37. *A cytological specimen classifier, comprising:*
   *a) microscope means for obtaining a view of at least part of a cytological specimen,*
   *b) camera means for creating an image of such view,*
   *c) image digitizing means for producing a digital representation of such image,*
   *d) a primary classifier for identification of objects in such digital representation based on a detectable feature, and*
   *e) secondary non-algorithmic classification means for recognition of cells having patterns typical of premalignant or malignant cells among the objects identified by the primary classifier.*

38. *The classifier of claim 37, wherein said secondary non-algorithmic classification means includes a neural network based classifier.*

39. *A method of classifying objects in a cytological specimen, comprising the steps of:*
   *a) obtaining a view of a cytological specimen,*
   *b) creating an image of such view,*
   *c) producing a digital representation of such image,*
   *d) primarily classifying objects in such digital representation of a cytological specimen based on a detectable feature, and*
   *e) secondarily classifying cells having features typical of premalignant or malignant cells among the objects identified in the primary classification step using non-algorithmic processing.*

40. *The method of claim 39, wherein the step of primarily classifying objects includes using an algorithmic classification.*

41. *A method of classifying objects in a cytological specimen, comprising the steps of:*
   *a) obtaining a view of a cytological specimen,*
   *b) creating an image of such view,*
   *c) producing a digital representation of such image,*
   *d) primarily classifying objects in such digital representation of a cytological specimen based on a detectable feature, and*
   *e) secondarily classifying cells having features atypical of cells expected in a normal specimen among the objects identified in the primary classification step using adaptive processing.*

* * * * *